United States Patent
Honda et al.

(10) Patent No.: US 8,711,347 B2
(45) Date of Patent: Apr. 29, 2014

(54) DEFECT INSPECTION METHOD AND DEVICE THEREFOR

(75) Inventors: Toshifumi Honda, Yokohama (JP); Yuta Urano, Yokohama (JP); Yukihiro Shibata, Fujisawa (JP); Toshiyuki Nakao, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/701,030

(22) PCT Filed: May 25, 2011

(86) PCT No.: PCT/JP2011/061953
§ 371 (c)(1),
(2), (4) Date: Jan. 24, 2013

(87) PCT Pub. No.: WO2011/152261
PCT Pub. Date: Dec. 8, 2011

(65) Prior Publication Data
US 2013/0114078 A1    May 9, 2013

(30) Foreign Application Priority Data
Jun. 3, 2010    (JP) .................. 2010-128029

(51) Int. Cl.
*G01N 21/00*    (2006.01)

(52) U.S. Cl.
USPC ........................................... 356/237.2

(58) Field of Classification Search
USPC ........................................... 356/237.2
See application file for complete search history.

(56) References Cited

U.S. PATENT DOCUMENTS

| 5,903,342 A | 5/1999 | Yatsugake et al. |
| 6,608,676 B1 | 8/2003 | Zhao et al. |
| 8,314,929 B2 * | 11/2012 | Urano et al. ............... 356/237.2 |
| 8,514,388 B2 * | 8/2013 | Maruyama et al. ........ 356/237.2 |
| 8,599,369 B2 * | 12/2013 | Urano et al. ............... 356/237.2 |
| 2005/0110988 A1 | 5/2005 | Nishiyama et al. |
| 2005/0185172 A1 | 8/2005 | Ishimaru et al. |
| 2006/0083470 A1 | 4/2006 | Solarz |
| 2006/0256325 A1 | 11/2006 | Mcmillan et al. |
| 2007/0070337 A1 | 3/2007 | Ohshima et al. |

FOREIGN PATENT DOCUMENTS

| JP | 9-304289 | 11/1997 |
| JP | 2003-21787 | 1/2003 |
| JP | 2003-130808 | 5/2003 |
| JP | 2004-233163 | 8/2004 |
| JP | 2005-156516 | 6/2005 |
| JP | 2006-201179 | 8/2006 |

(Continued)

*Primary Examiner* — Roy M Punnoose
(74) *Attorney, Agent, or Firm* — Antonelli, Terry, Stout & Kraus, LLP.

(57) ABSTRACT

Disclosed is a defect inspection method which makes it possible to scan the entire surface of a sample and detect minute defects without causing thermal damage to the sample. A defect inspection method in which a pulse laser emitted from a light source is subjected to pulse division and irradiated on the surface of a sample which moves in one direction while the divided-pulse pulse laser is rotated, reflection light from the sample irradiated by the divided-pulse pulse laser is detected, the signal of the detected reflection light is processed to detect defects on the sample, and information regarding a detected defect is output to a display screen, wherein the barycentric position of the light intensity of the divided-pulse pulse laser is monitored and adjusted.

16 Claims, 10 Drawing Sheets

(56) References Cited

FOREIGN PATENT DOCUMENTS

| | | | |
|---|---|---|---|
| JP | 2006-201179 | 8/2006 | |
| JP | 2006-201179 | 8/2006 | |
| JP | 2007-85958 | 4/2007 | |
| JP | 2008-511177 | 4/2008 | |
| WO | WO 2012/017761 A1 * | 2/2012 | ........... G01N 21/956 |

* cited by examiner

FIG. 3B

| NUMBER OF TIMES OF LIGHT TO ENTER POLARIZING BEAM SPLITTER 305 | LIGHT EMISSION TO RAY BUNDLE ENHANCING UNIT 5 SIDE | LIGHT REFLECTION TO MIRROR 306 |
|---|---|---|
| FIRST TIME | $\cos\theta$ | $\sin\theta$ |
| SECOND TIME | $\sin^2\theta$ | $\sin\theta, \cos\theta$ |
| THIRD TIME | $\sin^2\theta, \cos\theta$ | $\sin\theta, \cos^2\theta$ |
| FOURTH TIME | $\sin^2\theta, \cos^2\theta$ | $\sin\theta, \cos^3\theta$ |

FIG. 4

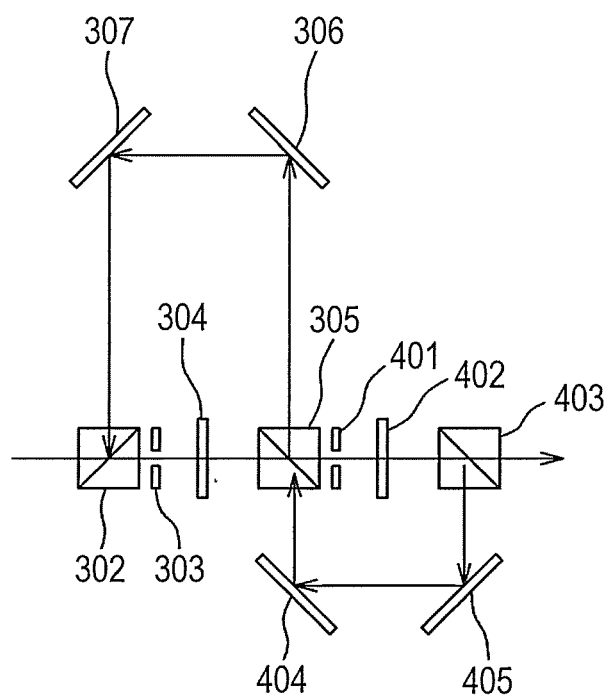

DEFECT INSPECTION METHOD AND DEVICE THEREFOR

TECHNICAL FIELD

The present invention relates to a defect inspection method and a device therefor that inspect micro defects on a sample surface and determine and output defect types and defect size.

BACKGROUND ART

In order to maintain and improve the yields of products in the manufacturing line of semiconductor substrates, thin film substrates, or the like, defects on the surfaces of semiconductor substrates, thin film substrates, or the like are inspected. In the conventional techniques for inspecting defects, Japanese Patent Application Laid-Open Publication No. Hei-9-304289 (Patent Literature 1), Japanese Patent Application Laid-Open Publication No. 2006-201179 (Patent Literature 2), and US Patent Application Publication No. 2006/0256325(Patent Literature 3), and so on are known. These are techniques in order to detect defects in which luminous light is focused on a sample surface in a size of a few dozen μm, the light is applied to the sample surface, and the light scattered from defects is focused and detected for inspecting defects in a size of a few dozen nm or more and a few μm or more. A stage, on which a sample (an inspection object) is held, is rotated, moved, and translated, so that the light spot is helically scanned on the sample surface, and the entire surface of the sample is inspected.

Moreover, Patent Literature 1 and Patent Literature 2 describe techniques in which a component emitted at a high angle and a component emitted at a low angle in light scattered from a defect are detected, and defect types are sorted according to ratios between the components.

Furthermore, Patent Literature 2 describes a technique in which the size of a detected defect is calculated based on the intensity of the light scattered from the defect.

In addition, Patent Literature 3 describes that the power of luminous light, the scan speed of a light spot, or the size of a light spot is controlled in inspecting an inspection object surface in order to reduce thermal damage to a sample. More specifically, Patent Literature 3 describes that it is assumed that thermal damage to a sample is determined by the product of light power density and irradiation time and the power of luminous light, the scan speed of a light spot, or the size of a light spot is changed according to the radial position on the sample being scanned in such a way that the product does not exceed a certain value.

Moreover, U.S. Pat. No. 6,608,676 (Patent Literature 4) is known as a technique in which a sample is illuminated in a wide range with a Gaussian beam long in one direction and illuminated regions are collectively detected using a multi pixel detector such as a CCD for inspecting the entire surface of the sample for a short time.

Furthermore, Patent Literature 5 describes a method in which in short-wavelength laser illumination, there are many pulse beam emission lasers in high power lasers, and in order to reduce thermal damage to a sample due to a sudden temperature rise in the sample caused by instantaneous light emission, an optical path is divided and a pulse is divided using differences between the lengths of the optical paths for reducing damage to the sample.

CITATION LIST

Patent Literature

Patent Literature 1: Japanese Patent Application Laid-Open Publication No. Hei-9-304289

Patent Literature 2: Japanese Patent Application Laid-Open Publication No. 2006-201179

Patent Literature 3: US Patent Application Publication No. 2006/0256325

Patent Literature 4: U.S. Pat. No. 6,608,676

Patent Literature 5: Japanese Patent Application Laid-Open Publication No. 2007-85958

SUMMARY OF INVENTION

Technical Problem

For defect inspection used in the manufacturing process steps of semiconductors or the like, the following is demanded: to detect micro defects, to highly accurately measure the size of a detected defect, to inspect a sample in a nondestructive manner (or without altering a sample), to obtain constant inspection results all the time in the case where the same sample is inspected (the number, positions, size, and defect types of detected defects), and to inspect a large number of samples within certain time, for example.

In the techniques described in Patent Literature 1, Patent Literature 2, and Patent Literature 4, scattered light from a defect is very weak particularly on micro defects in a size of 20 nm or less, and defect signals are buried in noise caused by the scattered light generated on the sample surface, in noise of the detector, or in noise of a detecting circuit, so that detection is infeasible. Alternatively, in the case where illuminating power is increased in order to avoid infeasible detection, a temperature rise in the sample due to luminous light is increased, and thermal damage to the sample occurs. Alternatively, in the case where the scan speed of a sample is reduced in order to avoid infeasible detection, the area of a sample or the number of samples that can be inspected within certain time is reduced. Thus, it was difficult to detect micro defects at high speed while avoiding thermal damage.

On the other hand, the technique described in Patent Literature 3 aimed to reduce thermal damage to the portion near the center of a sample, or to improve defect detecting sensitivity on the outer circumferential portion of a sample while suppressing thermal damage to the portion near the center of the sample to be equivalent to the conventional techniques, by changing illuminating power in proportion to the radial position on the sample as compared with the conventional techniques. This technique had the following problem because such an assumption was made that thermal damage is proportional to the product of irradiation power density and irradiation time.

First, since it is not taken into account of the influence of thermal diffusion from a light spot in estimating thermal damage, thermal damage to the center part of a sample where irradiation time is particularly long is excessively estimated more than real thermal damage. For this reason, illuminating power was reduced on the center part of the sample more than necessary, and defect detecting sensitivity was reduced.

Secondly, in order not to cause thermal damage on the entire surface of a sample, it is necessary to regulate input illuminating power based on the concept that no damage is caused to the center part of the sample where thermal damage is the maximum. However, since scan speed (linear velocity) was zero on the center part of the sample in rotation scanning, irradiation time according to calculations was diverged infinitely, thermal damage could not be quantitatively estimated based on the assumption, and illuminating power could not be regulated. On the contrary, in order to assure that thermal damage will not occur on the center part, it was necessary to make illuminating power zero, and the center part could not be inspected.

Thirdly, in the case of a pulse laser, the duration of a pulse is often about 15 ps. In a method in which a sample is inspected while rotating the sample, in the case where the sample is rotated at about 1,000 rpm, for example, a distance on which the sample moves for 15 ps is about 0.23 nm, and the sample can move on a very short distance with respect to optical resolution. Because of this, a region to which light is applied at a single pulse emission is almost determined according to the region of a beam spot, not according to the rate of travel at a position to which light is applied. Therefore, damage to the sample caused by an instantaneous temperature rise is rarely changed depending on the radial position on the sample.

Moreover, in Patent Literature 5, the optical path was divided into a plurality of optical paths using a polarizing beam splitter, light was guided to the optical paths in different optical path lengths, and timing, at which pulses reached in again guiding the light to the polarizing beam splitter for combining the optical paths according to the time difference when the light passed through the optical paths, was shifted for dividing the pulses. However, in the combining of the optical paths using the polarizing beam splitter, the combined light had a different polarization direction, so that such a configuration was inevitably provided in order to apply light in linear polarization in which a half of light intensity was shielded with a beam trap. Therefore, a higher output laser light source is necessary to apply light to a sample in the same light quantity. Generally, since it is necessary to resonate light in order to obtain high output using a laser light source, the frequency of a pulse becomes lower as output is more increased. Namely, the peak value per pulse tends to increase. In the method in which a half of light intensity is lost and a high output laser is inevitably used, the peak value itself of the light source itself was increased in many cases, and a sufficient effect could not be obtained.

Furthermore, in the method of Patent Literature 5, it was difficult to reduce a beam spot. Even though a beam spot with a small illuminating area is formed in the optical paths, the beam spots make a large beam spot as a whole when the light passing through the different optical paths is applied to the same location. A large number of mirrors are necessary to return the divided optical paths into the same optical path, and angular displacement generally occurs between the optical axes of beams in returning the divided optical paths into the same optical path with the polarizing beam splitter. For this reason, the light passing through the optical paths illuminates a different location, and a small beam spot cannot be obtained as a consequence. Since the light quantity obtained from a defect is determined according to the light quantity per unit area, an increase in the beam spot reduced defect detecting performance.

It is an object of the present invention to provide a defect inspection method and a device therefor that can scan the entire surface of a sample for a short time and detect micro defects with no thermal damage to the sample.

Solution to Problem

The present invention includes a pulse dividing unit formed of an optical dividing unit, a delay optical path, and an optical integrating unit, in which light emitted from a light source is adjusted to have a desired light quantity, the light is branched to a plurality of light beams at an optical branching unit, one of the branched light beams is guided to the delay optical path having a certain optical path length, and the light is again returned to a common optical path at the optical integrating unit. The present invention includes: an optical axis adjusting unit that expands the beam after passing through the pulse dividing unit to increase the absolute quantity of the axial displacement of the beam and to suppress fluctuations in the angles of the beams; and a light focusing unit arranged on the subsequent stage of the optical axis adjusting unit.

Moreover, in the present invention, in order to reduce damage to an optical element caused by the pulse dividing unit that passes the beam before expanded, the pulse dividing unit is entirely accommodated in a sealed container, and an inert gas such as nitrogen is filled in the container.

Furthermore, in the present invention, in order to apply the focused light to a sample, detect the reflected light and the scattered light at an optical sensor, and suppress the influence of fluctuations in non-uniform pulse intensity caused by the pulse dividing unit on the light detected at the sensor, a high-frequency signal removing circuit is included, which sufficiently suppresses fluctuations in the pulse caused by the pulse dividing unit based on the light emitting intensity.

In the present invention, a defect is detected because a signal value in a high-frequency band is large among signals passing through the high-frequency removing circuit.

Namely, in order to solve the problems, the present invention is a defect inspection device including: a table unit on which a sample is placed, the table unit being rotatable; a light source unit configured to emit a pulse laser; an illumination optical unit configured to divide a pulse of the pulse laser emitted from the light source unit to apply the divided-pulse pulse laser to the sample placed on the table unit; a detection optical unit configured to detect light reflected off the sample to which the divided-pulse pulse laser is applied by the illumination optical unit; a signal processing unit configured to process an output signal from the detection optical unit detecting the reflected light to detect a defect on the sample; and an output unit configured to output a result processed at the signal processing unit on a display screen. The illumination optical system unit includes: a pulse dividing unit configured to divide a pulse of the pulse laser emitted from the light source unit; a first beam monitor unit configured to monitor a barycentric position of light intensity of the divided-pulse pulse laser emitted from the pulse dividing unit; and a light intensity barycentric position adjusting unit configured to adjust the barycentric position of the light intensity of the divided-pulse pulse laser monitored at the first beam monitor unit.

Moreover, in order to solve the problems, the present invention is a defect inspection method including: dividing a pulse of a pulse laser emitted from a light source; applying the divided-pulse pulse laser to a surface of a sample moving in one direction while rotating the divided-pulse pulse laser; detecting light reflected off the sample to which the divided-pulse pulse laser is applied; processing a signal that the reflected light is detected to detect a defect on the sample; and outputting information about the detected defect on a display screen. A barycentric position of light intensity of the divided-pulse pulse laser is monitored, and the barycentric position of the light intensity of the monitored divided-pulse pulse laser is adjusted.

Advantageous Effect of Invention

According to the present invention, it is possible to scan the entire surface of a sample for a short time, and it is possible to detect micro defects with no thermal damage to the sample.

BRIEF DESCRIPTION OF DRAWINGS

FIG. 3B is a diagram of the list of the relationship between the amplitude of a pulse beam and the amplitude of a reflected pulse beam, the pulse beam transmitted through a polarizing beam splitter 305 in the pulse dividing unit for turns.

FIG. 4 is a block diagram of the configuration of the pulse dividing unit according to an embodiment of the present invention.

DESCRIPTION OF EMBODIMENTS

Figure 1A:
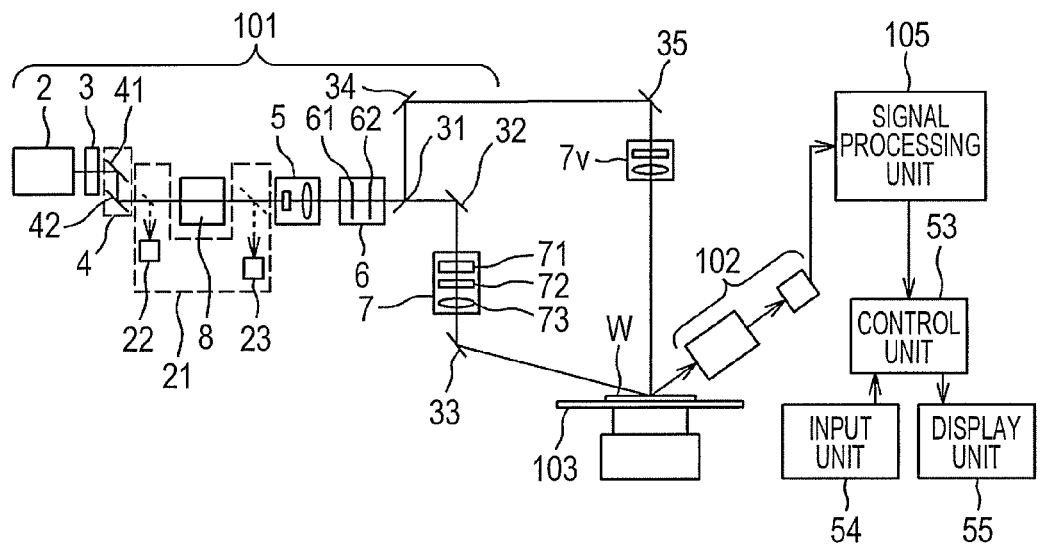
FIG. 1A is a block diagram of the overall schematic configuration of a defect inspection device according to an embodiment of the present invention.

A schematic configuration according to an embodiment of the present invention will be described with reference to FIG. 1. The schematic configuration includes an illuminating unit 101, a detecting unit 102, a stage 103 on which a sample W is placed, the stage 103 being rotatable in a direction perpendicular to the rotation center axis, a signal processing unit 105, a control unit 53, a display unit 54, and an input unit 55. The illuminating unit 101 includes a laser light source 2, an attenuator 3, an outgoing light adjusting unit 4, a pulse dividing unit 8, a laser light beam expanding unit 5, a polarization control unit 6, and a light focusing control unit 7. The laser light source 2 is a pulse oscillation laser or a quasi-continuous oscillation laser in which light emission time is typically 15 ps or less and pulsed laser is outputted at intervals of 10 ns. Moreover, the laser light source 2 outputs collimated laser beam. In the case of a laser light source that does not output collimated light, a collimating lens is separately provided to collimate the laser beam.

A laser beam emitted from the laser light source 2 is adjusted to have a desired beam intensity at the attenuator 3, and adjusted at the outgoing light adjusting unit 4 to provide a desired beam position and a beam traveling direction. The pulse dividing unit 8 divides a single pulse of pulsed laser into a plurality of time-divided pulses. The laser light beam expanding unit 5 expands the diameter of the laser light beam, and reduces fluctuations in the orientations of the laser light beam of the pulses divided at the pulse dividing unit. The polarization control unit 6 adjusts the laser light beam to have a desired polarized state. The light focusing control unit 7 adjusts the laser light beam to have a desired intensity distribution, and the laser light beam is applied to the inspection target region of the sample W. The pulse dividing unit 8 is a feature of the present invention. The beam is expanded at the laser light beam expanding units 5, whereas fluctuations in the angular direction of the optical axis of the time-divided pulse laser degrade light focusing performance at the light focusing control unit 7. Therefore, it is important to provide such a configuration in which the laser light beam expanding unit 5 is provided in the subsequent stage of the pulse dividing unit.

Generally, an illuminating shape on the sample is a rectangular shape of a high aspect ratio in order to reduce thermal damage at the minimum. Therefore, typically, for the light focusing control unit 7, the laser beam is shaped using two pairs of anamorphic prisms 71 and 72, and then applied through a condenser lens 73. Moreover, a diffractive optical element may be used instead of the condenser lens 73.

The incident angle of the laser beam to a sample surface (a slope angle to the normal direction of the sample surface) is determined according to the position and angle of a reflecting mirror 33 in the optical path of the illuminating unit 101. The incident angle of the laser beam is set at an angle suited to detect micro defects. The larger the light incident angle is, that is, the smaller the elevation angle (an angle formed between the sample surface and the optical axis of light) is, the weaker the scattered light (called haze) from micro roughness on the sample surface is; the scattered light from micro roughness becomes noise with respect to the scattered light from micro foreign substances on the sample surface. Thus, a large light incident angle is suited to detect micro defects. Therefore, in the case where scattered light from micro roughness on the sample surface hampers detecting micro defects, the incident angle of luminous light is set at an angle of 75 degrees or more (an elevation angle of 15 degrees or less).

On the other hand, since the absolute quantity of scattered light from micro foreign substances becomes larger as the light incident angle is smaller in grazing incidence illumination, in the case where a shortage of the quantity of light scattered from a defect hampers detecting micro defects, the incident angle of luminous light is set at an angle of 60 degrees or more and an angle of 75 degrees or less (an elevation angle of 15 degrees or more and 30 degrees or less). Moreover, in the case of conducting grazing incidence illumination, polarization is controlled by the polarization control unit 6 of the illuminating unit 101 to form the polarization of illumination to be P polarization, so that light scattered from a defect on the sample surface is increased more than other polarization.

The drive unit of a mirror 31, not illustrated, is used to insert the mirror 31 into the optical path of the illuminating unit 101, so that the illuminating optical path is changed, and luminous light is applied from a direction perpendicular to the sample surface (vertical illumination). At this time, the illuminating intensity distribution on the sample surface is controlled by a light focusing control unit 7v similarly in grazing incidence illumination. In order to obtain scattered light from concave defects on the sample surface (polished scratches or crystal defects of a crystal material), vertical illumination is suited, in which light substantially vertically enters the sample surface.

For the laser light source 2, in order to detect micro defects near the sample surface, such a laser light source is used in which an ultraviolet or vacuum ultraviolet laser beam at a short wavelength (a wavelength of 355 nm or less) with a high output of 2 W or more is oscillated as a wavelength that does not tend to penetrate the inside of the sample. The diameter of an outgoing beam is about 1 mm. In order to detect defects in the sample, such a laser light source is used in which a visible or infrared laser beam is oscillated as a wavelength that tends to penetrate the inside of the sample.

Figure 1B:
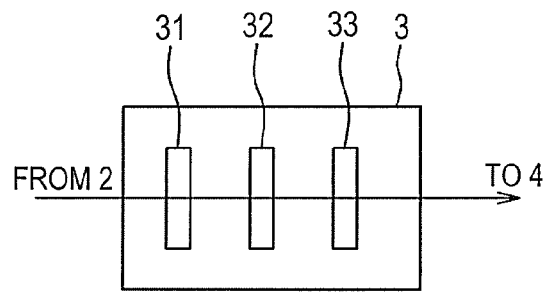
FIG. 1B is a block diagram of the configuration of an attenuator.

As illustrated in FIG. 1B, the attenuator 3 includes a first polarizer 31, a half-wave plate 32 rotatable about the optical axis of luminous light, and a second polarizer 33. Light incident to the attenuator 3 is converted into linear polarized light at the first polarizer 31, the polarization direction of the polarized light is rotated in a given direction according to the azimuth angle of the slow axis of the half-wave plate 32, and the polarized light passes through the second polarizer 33. The azimuth angle of the half-wave plate 32 is controlled to reduce light intensity at a given ratio. In the case where the degree of linear polarization of light incident to the attenuator 3 is high enough, the first polarizer 31 is not necessarily provided. For the attenuator 3, such an attenuator is used in which the relationship between the input signal and the neutral density ratio is calibrated beforehand. For the attenuator 3, an ND filter having gradation concentration distribution may be used.

The outgoing light adjusting unit 4 includes a plurality of reflecting mirrors. Here, an embodiment configured of two reflecting mirrors 41 and 42 will be described. Here, suppose that a three-dimensional rectangular coordinate system (XYZ coordinates) is defined, and incident light to the reflecting mirrors travels in the +X-direction. The first reflecting mirror 41 is disposed so as to deflect incident light in the +Y-direction (incidence and reflection in the XY-plane), and the second reflecting mirror 42 is disposed so as to deflect light that is reflected off the first reflecting mirror 41 in the +Z-direction (incidence and reflection in the YZ plane). At the reflecting mirrors 41 and 42, the position and traveling direction (the angle) of light emitted from the outgoing adjusting unit 4 are adjusted by translation and tilt angle adjustment. As descried above, the incidence and reflection surface (the XY plane) of the first reflecting mirror 41 is arranged orthogonal to the incidence and reflection surface (the YZ plane) of the second reflecting mirror 42, so that the position and angle of light emitted from the outgoing adjusting unit 4 (the light travels in the +Z-direction) can be independently adjusted in the XZ plane and in the YZ plane.

The detecting unit 102 is arranged in multiple units so as to detect scattered light from an illuminated region 20 in multiple directions. The arrangement of the detecting unit 102 for the sample W and the illuminated region 20 will be described with reference to FIG. 8.

Figure 8:
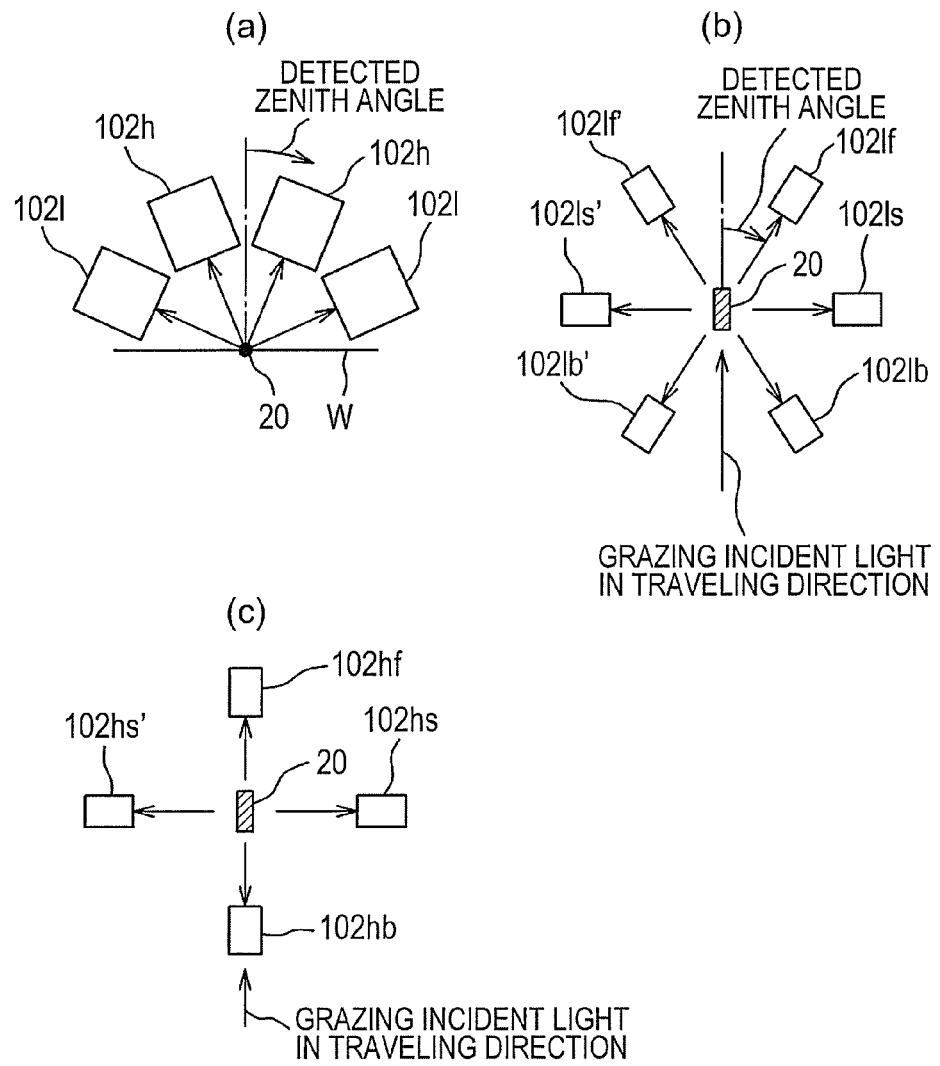
FIG. 8 is a block diagram of the configuration of the detecting unit according to an embodiment of the present invention.

FIG. 8(*a*) is a side view of the arrangement of the detecting unit 102. The illuminated region 20 has a long shape in a direction perpendicular to the paper surface of FIG. 8(*a*). An angle formed between the detecting direction (the center direction of a detection opening) of the detecting unit 102 and the normal of the sample W is defined as a detection zenith angle. The detecting unit 102 is formed of high-angle detecting units 102*h* with a detection zenith angle of 45 degrees or less and low-angle detecting units 102*l* with a detection zenith angle of 45 degrees or more. The high-angle detecting units 102*h* and the low-angle detecting units 102*l* are formed of a plurality of detecting units so as to cover scattered light scattering in multiple orientations at the detection zenith angles of the high-angle detecting units 102*h* and the low-angle detecting units 102*l*.

FIG. 8(*b*) is a plan view of the arrangement of the low-angle detecting units 102*l*. The illuminated region 20 has a long shape along the traveling direction of grazing incidence illumination illustrated by an arrow. An angle formed between the traveling direction of the grazing incidence illumination and the detecting direction is defined as a detection azimuth angle in a plane parallel with the surface of the sample W. The low-angle detecting unit 102 includes a low-angle front detecting unit 102*f*, a low-angle lateral detecting unit 102*s*, and a low-angle rear detecting unit 102*b*, and includes a low-angle front detecting unit 102*f'*, a low-angle lateral detecting unit 102*s'*, and a low-angle rear detecting unit 102*b'* located symmetrically to the light incident plane and the low-angle front detecting unit 102*f*, the low-angle lateral detecting unit 102*s*, and the low-angle rear detecting unit 102*b*. The low-angle front detecting unit 102*f* is disposed at a detection azimuth angle of zero degree or more and 60 degrees or less. The low-angle lateral detecting unit 102*s* is disposed at a detection azimuth angle of 60 degrees or more and 120 degrees or less. The low-angle rear detecting unit 102*b* is disposed at a detection azimuth angle of 120 degrees or more and 180 degrees or less.

FIG. 8(*c*) is a plan view of the arrangement of the high-angle detecting unit 102*h*. The high-angle detecting unit 102 includes a high-angle front detecting unit 102*f*, a high-angle lateral detecting unit 102*s*, and a high-angle rear detecting unit 102*b*, and includes a high-angle lateral detecting unit 102*s'* located symmetrically to the high-angle lateral detecting unit 102*s* with respect to the light incident plane. The high-angle front detecting unit 102*f* is disposed at a detection azimuth angle of zero degree or more and 45 degrees or less. The high-angle lateral detecting unit 102*s* is disposed at a detection azimuth angle of 45 degrees or more and 135 degrees or less. The high-angle rear detecting unit 102*b* is disposed at a detection azimuth angle of 135 degrees or more and 180 degrees or less.

Figure 2:
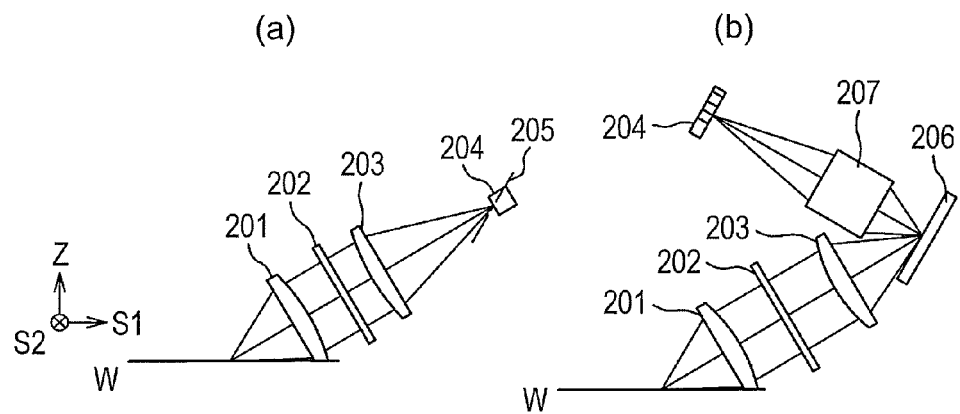
FIG. 2 is block diagrams of a detecting unit according to an embodiment of the present invention illustrating the layout and detecting direction of the detecting unit.

The specific configuration of the detecting unit 102 is illustrated in FIG. 2. The configurations of a low-angle detecting unit 102*ls* and a high-angle lateral detecting unit 102*hs* at a detection azimuth angle of 90 degrees (see FIGS. 8(*b*) and 8(*c*)) are illustrated in FIG. 2(*a*). Scattered light emitted from the illuminated region 20 is focused at an objective lens 201, and the light passes through a polarization filter 202. The light is guided at an image forming lens 203 to the light receiving surface of a multi pixel sensor 204, and detected. In order to efficiently detect scattered light, the detection NA of the objective lens 201 is 0.3 or more. In the case of the low-angle detecting unit, the lower end of the objective lens is cut off as necessary so as not to cause the lower end of the objective lens 201 to interfere with the surface of the sample W. The polarization filter 202 is formed of a polarizer or a polarizing beam splitter, and disposed so as to cut polarization components in an arbitrary direction. For the polarizer, a wire grid polarizer having a transmittance of 80% or more or the like is used. In the case of cutting an arbitrary polarization component including elliptically polarized light, the polarization filter 202 formed of a wave plate and a polarizer is disposed.

The multi pixel sensor 204 includes a plurality of photodetection pixels arranged linearly. In order to perform highly sensitive detection, the following photodetector is desirable: a photodetector of a high quantum efficiency (a high quantum efficiency of 30% or more) that can electrically amplify electrons after photoelectrically converted; photodetectors that can read signals from a plurality of pixels in parallel for high-speed processing; and a photodetector whose detection sensitivity (an electrically amplified gain) can be easily changed in a short time by using an electrical unit or the like for securing a detection dynamic range. For a photodetector satisfying the above conditions, the following is used: a multi-anode photomultiplier tube; an avalanche photodiode allay; a linear EMCCD (Electron Multiplying CCD) that can read signals in parallel; and a linear EBCCD (Electron Bombardment CCD) that can read signals in parallel. In the embodiment, the configuration using a multi-anode photomultiplier tube will be described.

The objective lens 201 and the image forming lens 203 form an image of the sample surface on a sample surface conjugate plane 205. Since an image tilted to the sample surface is formed, an object located at a large image height does not form an image on the light receiving surface of the multi pixel sensor 204 and blurs because of defocus in a scanning direction S1. However, the object located at a large image height does not affect detection because the size of the illuminated region 20 is short in the scanning direction S1.

FIG. 2(b) is the configurations of a low-angle front detecting unit 102*lf*, a low-angle rear detecting unit 102*hf*, a high-angle front detecting unit 102*lb*, and a high-angle rear detecting unit 102*hb*. Scattered light emitted from the illuminated region 20 is focused at the objective lens 201, the light passes through the polarization filter 202, and then an image of the sample surface (an intermediate image) is formed through the image forming lens 203 on a diffraction grating 206 disposed on the plane conjugate with the sample surface. The image of the sample surface formed on the diffraction grating 206 is projected onto the light receiving surface of the multi pixel sensor 204 with an image forming system 207 for detection. The multi pixel sensor 204 is disposed in the plane conjugate with the sample surface in such a way that the arranging direction of the pixels is matched with the longitudinal direction of the image in the illuminated region 20 as matched with the shape of the illuminated region 20 long in one direction. For the diffraction grating 206, in order to diffract the light that is guided by the image forming lens 203 and forms the intermediate image in the normal direction of the surface of the diffraction grating 206, a diffraction grating formed with a diffraction grating shape is used in which the Nth-order diffracted light of incident light along the optical axis of light that is guided by the image forming lens 203 and forms the intermediate image goes to the normal direction of the surface of the diffraction grating 206. A blazed diffraction grating is used for improving diffraction efficiency.

The multi pixel sensor 204 in the configuration above is disposed on the plane conjugate with the sample surface, so that an effective visual field can be secured in a wide range also in the direction S1 on the sample surface while suppressing defocus, and scattered light can be detected with a small loss of the light quantity.

Figure 1C:
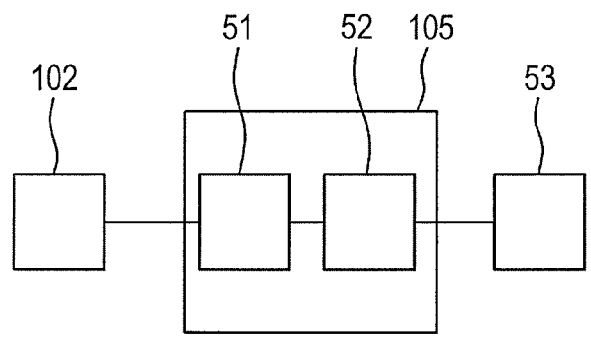
FIG. 1C is a block diagram of the configuration of a signal processing unit.
Figure 9:
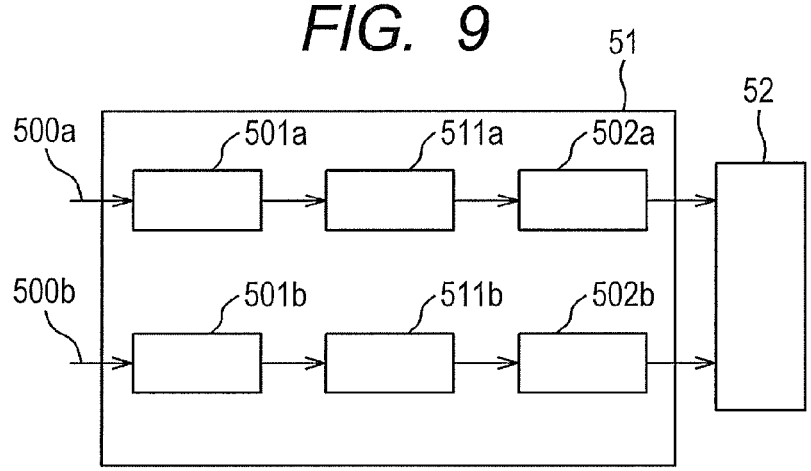
FIG. 9 is a block diagram of the configuration of an analog processing unit according to an embodiment of the present invention.

As illustrated in FIG. 1C, the signal processing unit 105 includes an analog processing unit 51 and a digital processing unit 52. The analog processing unit 51 will be described with reference to FIG. 9. Here, the configuration of the analog processing unit 51 will be described in the case of including two systems, a detecting unit 102a (corresponding to 102*ls* in FIG. 8) and a detecting unit 102b (corresponding to 102*hs* in FIG. 8) among the detecting units 102 for simplicity. Signal currents 500a and 500b outputted from the detectors (102*ls* and 102*hs* in FIG. 8) included in the detecting units 102a and 102b are converted into voltages at preamplifiers 501a and 501b and amplified. The high-frequency noise components of the amplified analog signals caused by uneven pulses at the pulse dividing unit 8, described later, are cut at low-pass filters 511a and 511b, and the amplified analog signals are then converted into digital signals at analog-to-digital converting units (A/D converting units) 502a and 502b having sampling rates higher than the cutoff frequencies of the low-pass filters 511a and 511b.

Figure 10:
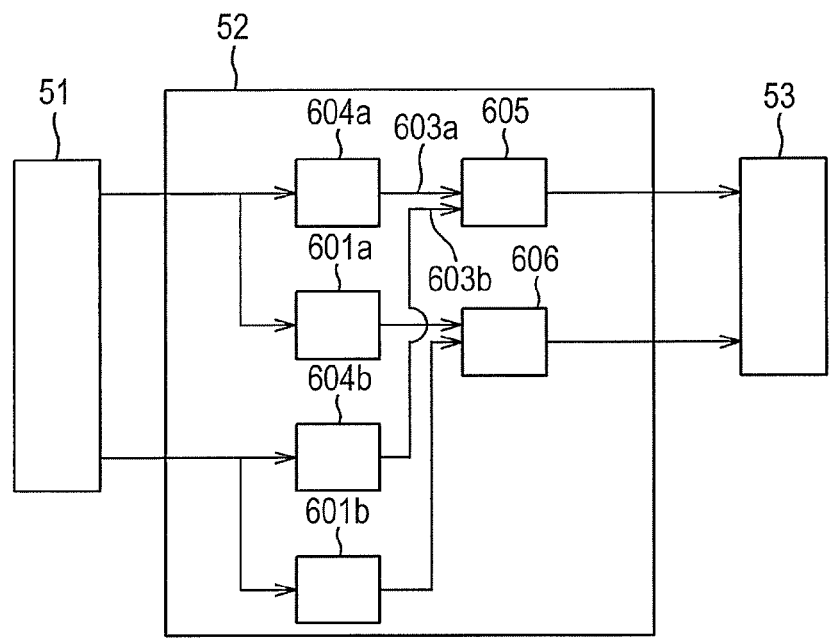
FIG. 10 is a block diagram of the configuration of a digital processing unit according to an embodiment of the present invention.

Next, the digital processing unit 52 forming the signal processing unit 105 will be described with reference to FIG. 10. Defect signals 603a and 603b are extracted from output signals from the analog processing unit 51 using high-pass filters 604a and 604b at the digital processing unit 52, and inputted to a defect determining unit 605. Since the defects are scanned by the lighting field 20 in the direction S1, the waveforms of the defect signals are ones that scale up or down the illumination distribution profile of the lighting field 20 in the direction S1. Thus, the high-pass filters 604a and 604b pass frequency bands including defect signal waveforms, whereas the high-pass filters 604a and 604b cut frequency bands in which a lot of noise is relatively included and direct current components, so that the signal-to-noise ratios of the defect signals 603a and 603b are improved. For the high-pass filters 604a and 604b, such filters are used: a high-pass filter or a band-pass filter having a specific cutoff frequency and designed to block components at the cutoff frequency or more; or a filter analog to the waveforms of the defect signals in which the shape of the illuminated region 20 is reflected.

The defect determining unit 605 applies threshold processing to the input of signals including defect waveforms outputted from the high-pass filters 604a and 604b, and determines the presence or absence of defects. Namely, since defect signals based on the detected signals from a plurality of detection optical systems are inputted to the defect determining unit 605, the defect determining unit 605 can inspect defects highly sensitively as compared with defect detection based on a single defect signal by applying threshold processing to the sum or weighted mean of defect signals, or by finding ORs or ANDs of defect groups extracted through applying threshold processing to the defect signals on the same coordinate system set on the surface of a wafer, for example.

Moreover, the defect determining unit 605 presents, as defect information to the control unit 53, defect coordinates indicating the position of a defect in a wafer and the estimated value of the defect size calculated based on the defect waveform and the sensitivity information signal at a location at which it is determined that the defect exists, and outputs the defect coordinates and the estimated value to the display unit 54 or the like. The defect coordinates are calculated based on the barycenter of a defect waveform. The defect size is calculated based on the integral value or the maximum value of a defect waveform.

Furthermore, output signals from the analog processing unit 51 are inputted to low-pass filters 601a and 601b in addition to the high-pass filters 604a and 604b forming the digital processing unit 52, and the low-pass filters 601a and 601b output low frequency components and direct current components corresponding to the quantity of scattered light (haze) from micro roughness in the illuminated region 20 on the wafer. As described above, the outputs from the low-pass filters 601a and 601b are inputted to a haze processing unit 606 to process haze information. Namely, the haze processing unit 605 outputs signals corresponding to the sizes of haze at locations on the wafer as haze signals based on the magnitudes of input signals obtained from the low-pass filters 601a and 601b. In addition, since the angular distribution of the scattered light quantity from the roughness is varied according to the spatial frequency distribution of micro roughness, the haze signals from the detectors of the detecting units 102 disposed in different azimuth angles or different elevation angles as illustrated in FIG. 8 are inputted to the haze processing unit 606, so that information about the spatial frequency distribution of micro roughness can be obtained from the haze processing unit 606 from the intensity ratios or the like.

The pulse dividing unit 8 will be described with reference to FIG. 3A. The pulse dividing unit is accommodated in a seal-structured container 312 denoted by 312. 300 denotes luminous light emitted from the outgoing light adjusting unit 4, which is collimated light. The luminous light 300 is controlled by a half-wave plate 301 in such a way that the polarization direction is a polarization direction in which the luminous light 300 passes through a polarizing beam splitter 302. The polarization direction of the luminous light is controlled in such a way that the luminous light passes through the polarizing beam splitter 302 and an aperture 303, and then the luminous light is branched at a polarizing beam splitter 305 through a half-wave plate 304. Light in a specific polarization direction is emitted from the polarizing beam splitter 305. In the case where the polarization direction is shifted from the transmission direction of light by e due to the half-wave plate 304, the amplitude and intensity of light to be emitted is $\cos\theta$ times those of inputted light. Light in the polarization direction orthogonal to the emitted light is branched at the polarizing beam splitter 305, reflected off by the mirrors 306 and 307, and guided to the polarizing beam splitter 302.

For the amplitude of the light branched at the polarizing beam splitter 305 and guided to the mirror 306, the polarization direction of 304 is expressed by sine using $\theta$. The light guided by the polarizing beam splitter 302 is totally reflected off by the polarizing beam splitter 302, and polarized at the half-wave plate 304. The amplitude of light sine times the amplitude of the light reflected off by the polarizing beam splitter 302 and incident to the polarizing beam splitter 305 is emitted, and other light, that is, light having the amplitude $\cos\theta$ times the light incident to 305 is branched in the direction of the mirror 306.

As described above, the light passing through the mirrors 306 and 307 first has the amplitude of sine of the light incident to 305. The light intensity is then reduced at turns as:

the second turn: $\sin\theta\cdot\cos\theta$, and the third turn: $\sin\theta\cdot\cos 2\theta$.

FIG. 3B is the relationship between the quantity of light emitted from the polarizing beam splitter 305 and the quantity of light reflected to the mirror 306 for turns.

It is noted that energy is not lost by branching light at the beam splitter.

In order to minimize damage to the sample, the polarizing beam splitter 305 is necessary to minimize the maximum value of the intensity of light branched and passing in the direction of the laser light beam expanding unit 5. This maximum value is a pulse that first passes or a second pulse. Therefore, it is shown that the condition that the light intensity of the first pulse is made equal to the light intensity of the second pulse is the best condition that no damage is caused to the sample.

Namely, the condition is:

$$\cos\theta=\sin\theta\cdot\sin\theta.$$

It is shown that $\theta$ is an angle of 51°, and the amplitude is about 62% of input, which is converted into energy of 38.1%. Conversely, since no damage is caused to the sample even though the output of the laser light source is made $1/0.381=2.6$ times, the sensitivity of the device can be greatly improved. The optical energies of the third pulse and the fourth pulse are suddenly reduced to 14.6% in the third pulse and 6% in the fourth pulse.

Next, the optical path length necessary to divide a pulse will be described. In the case of analyzing a phenomenon that heat is increased due to pulse-like light, suppose that the pulse is about 16 ps, for example, it is 88 mm$^2$/S in the case of a silicon sample, for example, a spread of heat in the depth direction is several tens of nanometers, and heat spreads extremely on the surface layer. Therefore, the heat spread can be expressed by a one-dimensional model. The heat spreads in the depth direction at a speed of about the 0.5th power of time, and the peak temperature is approximated when the peak temperature is inversely proportional to the spread. For example, when the intensity of a pulse is $\frac{1}{25}$, and light emission time is 25 times, that is, time of about 400 ps elapses, the temperature is $\frac{1}{5}$. In the case where the intensity of a pulse is the same and the light emission interval is 25 times, the temperature is greatly reduced below $\frac{1}{5}$. Since the distance on which light travels for 400 ps is about 12 cm, it is shown that the distance from the polarizing beam splitter 305 to the polarizing beam splitter through the mirrors 306 and 307 may be about 12 cm.

308 and 309 denote position control mechanisms that control the positions of the mirrors 306 and 307, respectively. 310 and 311 denote rotation control mechanisms that control the rotation angle of the half-wave plate. 312 denotes a cover that blocks the pulse dividing unit from outside air, and supplies dry air from 313 through a filter and exhausts air from 314. For dry air, an inert gas such as a nitrogen gas or a carbon dioxide gas is desirable. Thus, since luminous light passes inside the cover 312 in a relatively small beam diameter, dust or the like is prevented from attaching the mirror, causing chemical reaction, and displacing the optical axis.

Figure 3A:
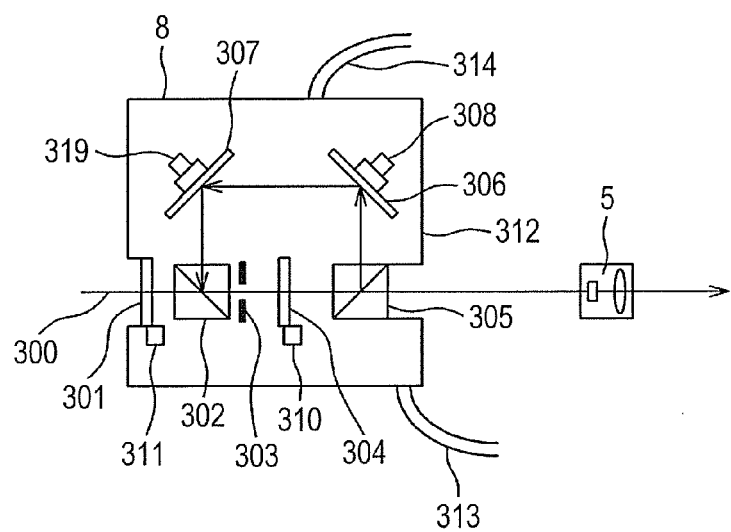
FIG. 3A is a block diagram of the configuration of a pulse dividing unit.

In order to apply a larger light quantity to the pulse dividing unit illustrated in FIG. 3A with no damage to the sample, it is necessary to more finely divide a pulse. This embodiment is illustrated in FIG. 4. Optical elements used from the polarizing beam splitter 302 to the mirror 307 through the polarizing beam splitter 305 are the same as the optical elements illustrated in FIG. 3A. 401 denotes an aperture, 402 denotes a half-wave plate, 403 denotes a polarizing beam splitter, and 404 and 405 denote mirrors. The optical path length of the optical path from the polarizing beam splitter 305 to the polarizing beam splitter 302 through the mirror 306 and the mirror 307 is set over 3 times the optical path length illustrated in FIG. 3.

On the other hand, the optical path length of the optical path from the polarizing beam splitter 403 to the polarizing beam splitter 305 through the mirror 405 and the mirror 404 is set to the length nearly equal to the optical path length of the optical path from the polarizing beam splitter 305 to the polarizing beam splitter 302 through the mirrors 306 and 307 in FIG. 3. It is noted that although not illustrated in FIG. 4, the mirrors 306, 307, 404, and 405 include position control mechanisms that adjust the angles of the mirrors corresponding to the position control mechanisms 308 and 309 described in FIG. 3A. Moreover, the half-wave plates 304 and 402 include angle control mechanisms that can rotate at an angle as described in FIG. 3A.

Figure 5:
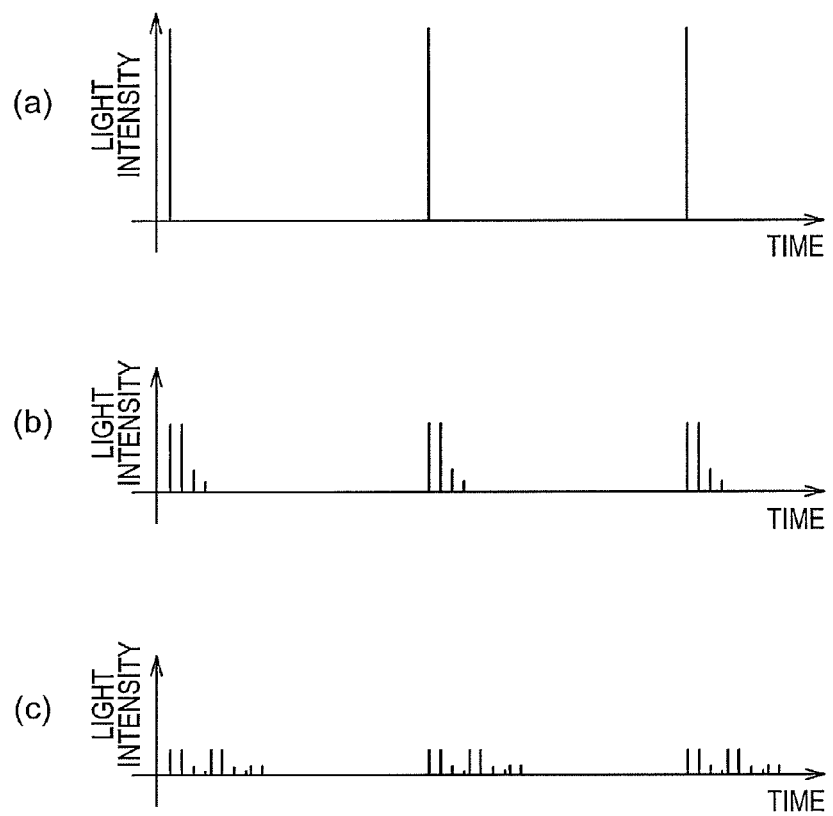
FIG. 5(a) is a diagram of the light intensity of a pulse laser incident to the pulse dividing unit according to an embodiment of the present invention.
FIG. 5(b) is a diagram of the light intensity of a divided pulse beam outputted from the pulse dividing unit in the configuration in FIG. 3A.
FIG. 5(c) is a diagram of the light intensity of a divided pulse beam outputted from the pulse dividing unit in the configuration in FIG. 4.

Divided pulses in the case where the optical path in FIG. 4 is set are illustrated in FIG. 5. The rotation angle of the half-wave plate that minimizes light intensity is the same as the rotation angle of the pulse dividing unit in FIG. 3A, and θ is an angle of 51°. FIG. 5(a) illustrates light intensity outputted from the light source. FIG. 5(b) illustrates light intensity outputted from the pulse dividing unit according to the embodiment illustrated in FIG. 3A. FIG. 5(c) illustrates light intensity from the pulse dividing unit according to the embodiment illustrated in FIG. 4. The maximum value of light intensity in FIG. 5(c) is 14.5% of light intensity in FIG. 5(a). As described above, the pulse dividing unit according to the present invention cannot obtain pulses of uniform intensity, and pulse intensity fluctuates every time. Therefore, the low-pass filters 511a and 511b described above determine the cutoff frequency so as not to pass the band where the intensity of the divided pulse fluctuates.

Since the ununiformity of the intensity of harmonics occurs at higher frequencies than the oscillation pulse frequency of a laser emitted from the laser light source 2, the cutoff frequency may be made smaller than the oscillation pulse frequency of the laser light source 2. Moreover, as a result, the sampling frequencies of AD converting units 502a and 502b may be ½ of the oscillation pulse frequency of the laser light source 2 or less based on the Nyquist theorem.

The laser light beam expanding unit 5 includes two lens groups or more, and has a function that expands the diameter of an incident collimated beam. FIG. 1A is an example of a Galileo beam expander including a combination of a concave lens 501 and a convex lens 502. The laser light beam expanding unit 5 is disposed on a translation stage with two axes or more (not shown), in which the position can be adjusted in such a way that the center is matched with a predetermined beam position. Moreover, a tilt angle adjusting functional mechanism (not shown) is provided for adjusting a tilt angle of the laser light beam expanding unit 5 in such a way that the optical axis of the laser light beam expanding unit 5 is matched with the optical axis of a beam from the pulse dividing unit 8 to the deflection control unit 6. The interval between the concave lens 501 and the convex lens 502 is adjusted to control the magnification of the laser light beam diameter (a zooming mechanism).

The magnification of the beam diameter by the laser light beam expanding unit 5 ranges from 10 to 20 times, and a beam emitted from the light source 2 and having a diameter of 1 mm is expanded in the range of a diameter of about 10 to 20 mm. In the expansion, the slopes of the optical axes of the divided pulses caused by time-dividing a single pulse at the pulse dividing unit 8 are reduced from 1/10 to 1/20 on the contrary. For example, suppose that fluctuations in the slopes of the optical axes of the divided pulses emitted from the pulse dividing unit 8 are about 100 μrad, fluctuations in the divided pulse beams emitted from the laser light beam expanding unit 5 range from 5 to 10 μrad.

The polarization control unit 6 is configured to include a half-wave plate 61 and a quarter-wave plate 62, and controls the polarized state of luminous light to be a given polarized state.

Figure 6:
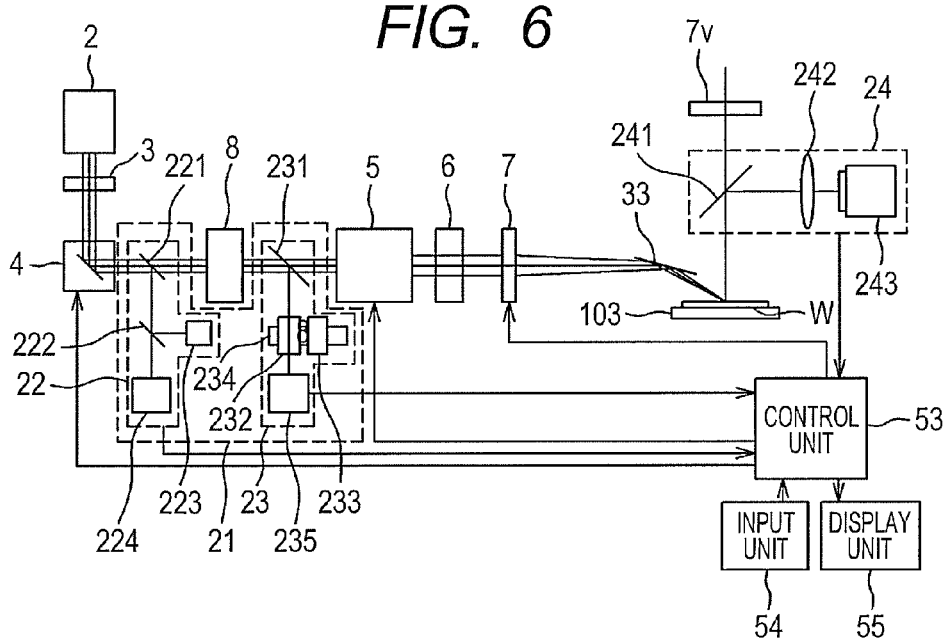
FIG. 6 is a block diagram of the schematic configuration of an illuminating unit of the defect inspection device according to an embodiment of the present invention including a beam monitoring unit.

An illumination light state measuring unit 21 that measures the states of light emitted from the outgoing light adjusting unit 4 and light emitted from the pulse dividing unit 8 in the midway point of the optical path of the illuminating unit 101 will be described with reference to FIG. 6. The illumination light state measuring unit 21 is configured to include beam monitors 22 and 23. The beam monitor 22 measures and outputs the position and angle (the traveling direction) of luminous light passing through the outgoing light adjusting unit 4. The beam monitor 23 measures and outputs the position of luminous light emitted from the pulse dividing unit 8.

The position of luminous light is measured at the beam monitor 22 by measuring the barycentric position of the light intensity of luminous light. For a concrete position measuring unit, a position sensitive detector (PSD) 223, or an image sensor such as a CCD sensor and a CMOS sensor is used. A part of illumination light passing through the outgoing light adjusting unit 4 is branched at a half mirror 221, and a part of illumination light passing through the outgoing light adjusting unit 4 and branched at this half mirror 221 is branched at a half mirror 222 and detected. The angle of the illumination light is measured at the beam monitor 22 by detecting light transmitted through the half mirror 222 using a position sensitive detector or an image sensor 224 located far from the light source with the position measuring unit. The position of luminous light and the angle of illumination light measured at the beam monitor 22 are inputted to the control unit 53, and displayed on the display unit 55. In the case where the position or angle of illumination light is shifted from a predetermined position or angle, illumination light is adjusted at the outgoing light adjusting unit 4 so as to return to a predetermined position.

The position of illumination light is measured at the beam monitor 23, in which a part of illumination light passing through the pulse dividing unit 8 is branched at a half mirror 231, the branched light is switched to a focus optical system 232 or an image forming optical system 233 at an optical system switching unit 234, and the light is detected at an image sensor 235 such as a CCD sensor and a CMOS sensor to measure the barycentric position of the light intensity of illumination light.

Figure 7:
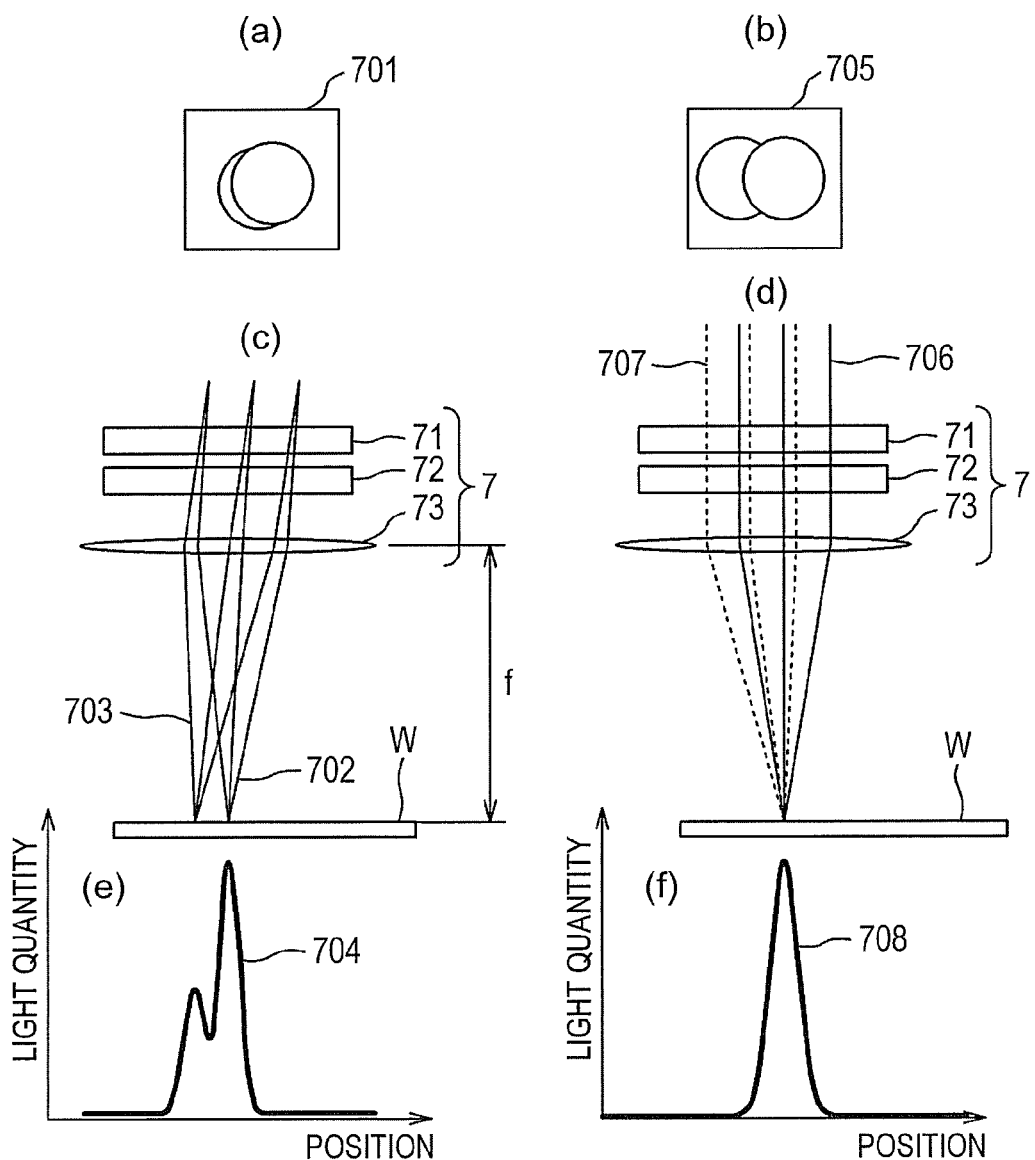
FIG. 7 is a diagram of the light focusing characteristics of the illuminating unit according to an embodiment of the present invention.

When the optical axis is shifted at the pulse dividing unit 8, it is difficult to focus light on the sample by the light focusing control unit 7. This will be described with reference to FIG. 7. In FIG. 7, 701 in FIG. 7(a) and 705 in FIG. 7(b) are two-dimensional light quantity distribution detected at the beam monitor 23. The light focusing control unit 7 is configured to include two pairs of anamorphic prisms 71 and 72 and a condenser lens 73.

FIG. 7(c) illustrates a state in which a laser light beam 702 of a pulse (a first divided pulse) from the pulse dividing unit 8 that the optical path is not branched and a laser light beam 703 of a second divided pulse passing through an optical path branched at the pulse dividing unit 8 (an optical path from the polarizing beam splitter 305, to the mirror 306, to the mirror 309, to the polarizing beam splitter 302 and again to the polarizing beam splitter 305) enter almost the same position at the light focusing control unit 7, but incident angles to the sample W through the light focusing control unit 7 are different.

FIG. 7(d) illustrates a state in which the positions of a first divided pulse 706 incident to the light focusing control unit 7 and a second divided pulse 707 are different but the directions incident to the sample W through the light focusing control unit 7 are the same.

When light incident to the light focusing control unit 7 is a collimated beam, as illustrated in a profile 704 in FIG. 7(e) and a profile 708 in FIG. 7(f), for the light focusing state on the sample, fluctuations in the angle of the laser light beam incident to the condenser lens 73 are more important to focus light on the sample W than fluctuations in the laser light beam at the position on the main surface of the condenser lens 73. For example, in the case where the difference between the incident angles of the divided pulse beams to the lenses is $\Delta\phi$ and the focal length of the condenser lens 73 is f, the position on the sample W to which these two divided pulse beams are applied is shifted by about $f\cdot\Delta\phi$. Therefore, it is important to make $\Delta\phi$ smaller. For example, in the case where light emitted from the laser light beam expanding unit 5 has 5 μrad of $\Delta\phi$, the light can be focused within a displacement of about 0.5μm, where f is 100 mm.

The beam monitor 23 is provided to observe $\Delta\phi$. The image sensor 235 such as a CCD sensor and a CMOS sensor is used for the detector of the beam monitor 23, and such a setting is made in which collimated light is focused on this image sensor 235 through the light focusing optical system 232, and then the obtained image is almost equal to an image enlarged by the magnification of the laser light beam expanding unit 5 with respect to the pattern on the sample surface. This mode is referred to as a focus acquiring mode. Moreover, such a configuration is provided in which the optical system switching unit 234 can switch between the light focusing optical system 232 and the image forming optical system 233 in such a way that the detector 235 of the beam monitor 23 can also form an image of the pattern of a laser light beam immediately before entering the laser light beam expanding unit 5 through the image forming optical system 233. The mode that acquires an image of the laser light beam pattern is referred to as a laser beam pattern monitoring mode.

For the beam monitor 23, such a configuration is described in which the optical system switching unit 234 switches between the light focusing optical system 232 and the image forming optical system 233 for the modes and an image is shot using a single detector 235. However, such a configuration may be possible in which the combinations of the optical system and the detector are separately provided to branch the optical path and images can be shot in two modes at the same time. Moreover, such a configuration may be possible in which the optical system is devised to acquire images in two modes at the same time using a single detector.

The illuminating intensity distribution on the surface of the sample W adjusted at the light focusing control unit 7 is monitored by measuring the illuminating intensity distribution on the optical axis of the light focusing control unit 7v for vertical illumination using an illuminating intensity distribution monitor 24. In the illuminating intensity distribution monitor 24, an image of light reflected from the surface of the sample W and reflected by a half mirror 241 arranged on the optical axis of the light focusing control unit 7v is formed on an image sensor 243 such as a CCD sensor and a CMOS sensor through a lens 242, and detects the reflected light as an image. The image of the illuminating intensity distribution detected at the illuminating intensity distribution monitor 24 is processed at the control unit 53 to calculate the barycentric position of intensity, the maximum intensity, the position of maximum intensity, the width and length of the illuminating intensity distribution (the width and length of an illuminating intensity distribution region at a predetermined intensity or more or at a predetermined ratio or more to the maximum intensity value) or the like, and the values are displayed on the screen of the display unit 55 together with the outline and shape of the illuminating intensity distribution and the cross sectional waveform, for example.

Figure 11:
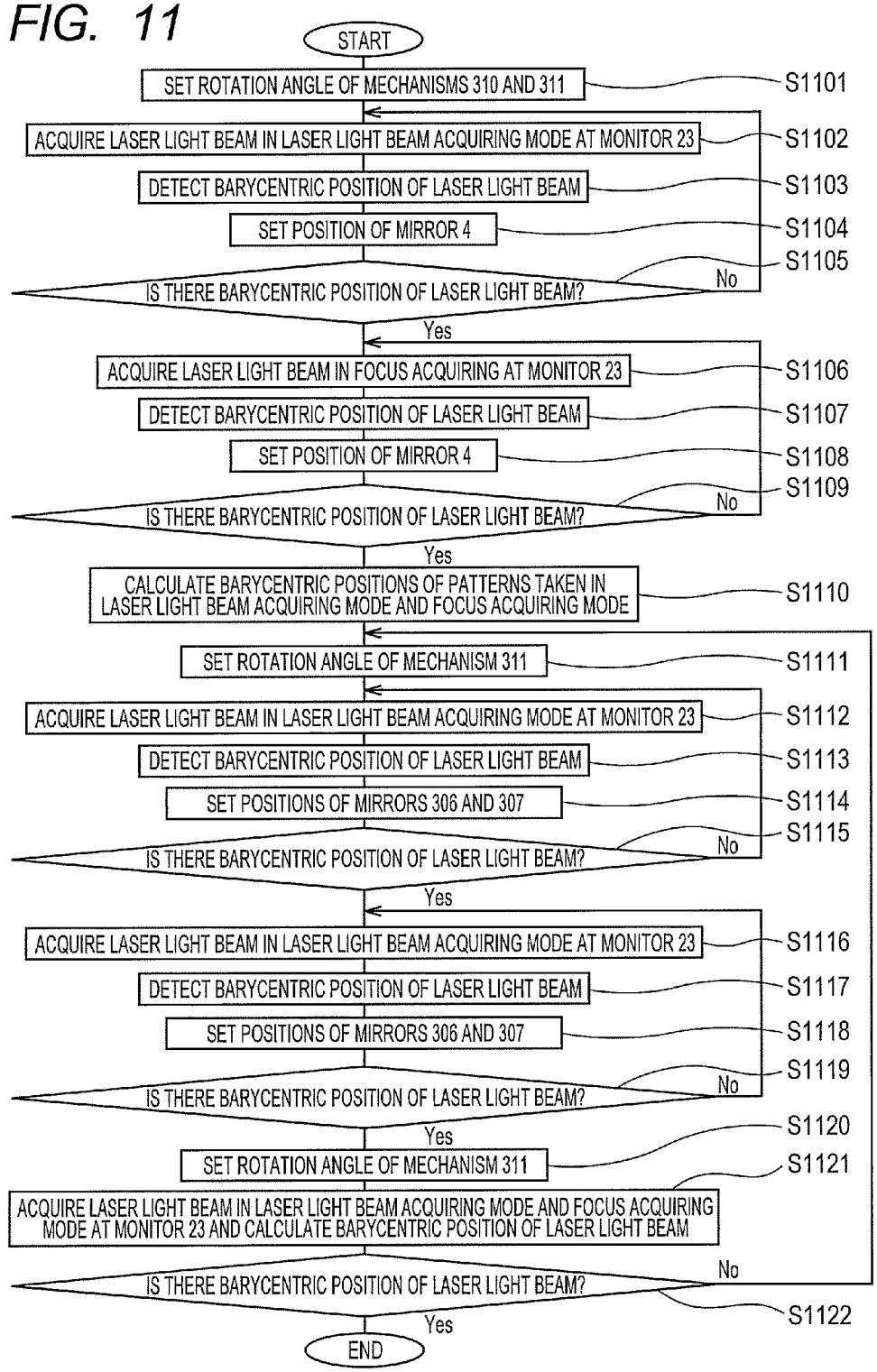
FIG. 11 is a sequence diagram of the procedures of adjusting the optical system of the pulse dividing unit according to an embodiment of the present invention.

A method for adjusting the mirrors 41, 42, 306, and 307 using the beam monitor 23 will be described with reference to FIG. 11. Here, in the configuration illustrated in FIG. 3A, first, the rotation control mechanisms 310 and 311 that control the rotation angles of the half-wave plates 301 and 304 are set in a state (A) in which all the light incident to the pulse dividing unit 8 is outputted, not branched at the polarizing beam splitters 302 and 305 (S1101). The beam monitor 23 is set in the laser beam pattern monitoring mode to acquire a laser light beam pattern (S1102), and the barycentric position of a bright spot is calculated at the control unit 53 (S1103). The mirrors 41 and 42 of the outgoing light adjusting unit 4 are controlled to automatically adjust the optical axis based on the result in such a way that the laser light beam passes through the center position of the optical system at the laser light beam expanding unit 5 (S1104). The angles of the mirrors 41 and 42 in adjusting the optical axis can be easily determined according to a generally known geometric-optical method. The steps are performed until the barycentric position of the laser light beam comes to a desired position (S1105).

Subsequently, the optical system switching unit 234 adjusts the light focusing optical system 232 in such a way that the light focusing optical system 232 is located on the detection optical axis of the detector 235, and the beam monitor 23 is set in the focus acquiring mode to acquire an image (S1106). The control unit 53 again calculates the barycentric position of the bright spot (S1107), and the control values of the mirrors 41 and 42 at which the beam is focused at a predetermined position in the focus mode are calculated while maintaining the conditions that the laser light beam enters the center of the beam expanding unit 5. The angles of the mirrors 41 and 42 are automatically set in such a way that the mirrors 41 and 42 are in this state (S1108). The operations from S1106 to S1109 are repeated until the barycentric position of light comes to a desired position (S1109). Moreover, the control unit 53 controls the optical system switching unit 234 in the state in which the angles of the mirrors 41 and 42 are set, the image forming optical system 233 acquires the laser light beam pattern in the laser light beam pattern monitoring mode, and the light focusing optical system 232 acquires the laser light beam pattern in the focus acquiring mode. The barycentric positions of the laser light beam in the laser beam pattern monitoring mode and the focus acquiring mode are determined from the shot laser light beam patterns, and the barycentric positions are stored (S1110).

Subsequently, the rotation control mechanism 311 is set in a mode in which all the light is transmitted through the polarizing beam splitter 302, branched at the polarizing beam splitter 305, in turn reflected off the mirrors 306 and 307, and again reaches the beam splitter 302 (S1111). The control unit 53 controls the optical system switching unit 234 to switch between the light focusing optical system 232 and the image forming optical system 233 in this state, and the image forming optical system 233 sets the beam monitor 23 again in the laser light beam pattern monitoring mode to acquire the laser light beam (S1112). The control unit 53 calculates the barycentric position of the bright spot (S1113), the angles of the mirrors 306 and 307 are calculated at which the laser light beam is matched with the pattern in the laser light beam pattern monitoring mode in the state A based on the result, and the angles of the position control mechanisms 308 and 309 are automatically set in such a way that the angles are at the calculated angles (S1114). The steps are repeated until the barycentric position of light comes to a desired position (S1115).

The angles can also be determined geometric-optically. It is noted that in the case where the total light quantity of the obtained patterns is lower than the expected value, it is likely that the laser light beam does not pass through the center of the aperture 303. Thus, different angles are set for a plurality of times under the conditions that the barycentric position of the bright spot is not changed, and the mirrors 306 and 307 are set at angles to produce the maximum brightness.

Subsequently, the control unit 53 controls the optical system switching unit 234 to switch between the image forming optical system 233 and the light focusing optical system 232, and the light focusing optical system 232 changes the beam monitor 23 in the focus acquiring mode to acquire the laser light beam in the focus acquiring mode in the state A (S1116). The barycentric position of the laser light beam is calculated (S1117), the angles of the mirrors 306 and 307 are calculated in such a way that the barycentric position is matched with the barycentric position in the focus acquiring mode calculated in S1110, and the angles of the position control mechanisms 308 and 309 are automatically set in such a way that the angles are at the calculated angles (S1118). The steps are repeated until the barycentric position of light comes to a desired position (S1119).

Figure 12:
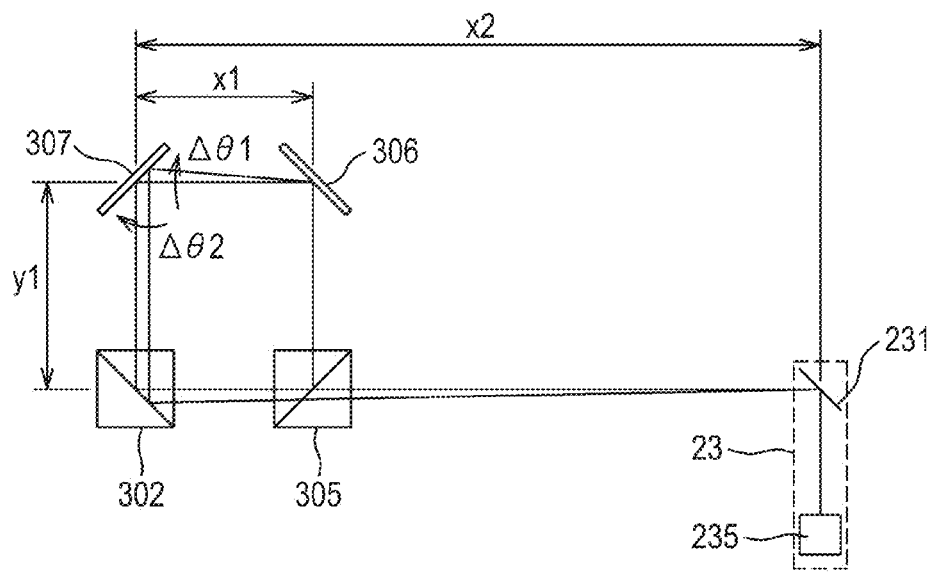
FIG. 12 is a block diagram of the pulse dividing unit including a beam monitoring unit according to an embodiment of the present invention, illustrating the relationship between the angle of a mirror and input fluctuations in a laser light beam expanding unit.

FIG. 12 illustrates a state in which the laser light beam enters a determined position but the angle is different at the incident portion of the laser light beam expanding unit 5 in the laser light beam imaging mode of the beam monitor 23. In the case where the laser light beam is shifted by $\Delta\theta 1$ at the mirror 306 and by $\Delta\theta 2$ at the mirror 307 from ideal mirror positions, a displacement from the ideal optical axis at the laser light beam expanding unit 5, $\Delta y$, which is a displacement from a desired optical axis position, can be approximated by the following equation when $\Delta\theta 1$ and $\Delta\theta 2$ are small.

$$\Delta y = 2((y1+x2)\Delta\theta 2 - (x1+y1+x2)\Delta\theta 1)$$

In the laser light beam pattern monitoring mode, a distance proportional to $\Delta y$ can be detected as the displacement of the barycentric position.

Here, x1 is a distance between the mirrors 306 and 307, y1 is a distance between the mirror 307 and the polarizing beam splitter 302, and x2 is a distance from the polarizing beam splitter 302 to the beam expanding unit.

On the other hand, in the case of the focus acquiring mode, an amount proportional to the displacement $\Delta y2$ from a desired position is observed, and this value is expressed by the following equation.

$$\Delta y2 = \Delta\theta 2 - \Delta\theta 1$$

Therefore, the displacements $\Delta\theta 1$ and $\Delta\theta 2$ of the mirrors are calculated to set the mirrors at desired positions. Moreover, since desired optical axes are sometimes not completely adjusted because the equations include approximations, or the values x1, x2 have errors, and y1, for example, the laser light beam pattern monitoring mode and the focus acquiring mode are again set, and adjustment is repeated until a desired error range is achieved.

Moreover, lastly, the angle of the rotation control mechanism 311 is set at an angle at which the maximum value of the light intensity of a single pulse takes the smallest value (S1120), the laser light beam pattern monitoring mode and the focus acquiring mode are set to acquire the laser light beam, and the barycentric position is calculated (S1121). In the case where the position is different from the position calculated in S1110, the positions of the mirrors are again adjusted from S111 (S1122). In the case where the position is matched with the laser light beam position calculated in S1110, an image of the laser light beam is shot, and this image is stored.

Figure 13:
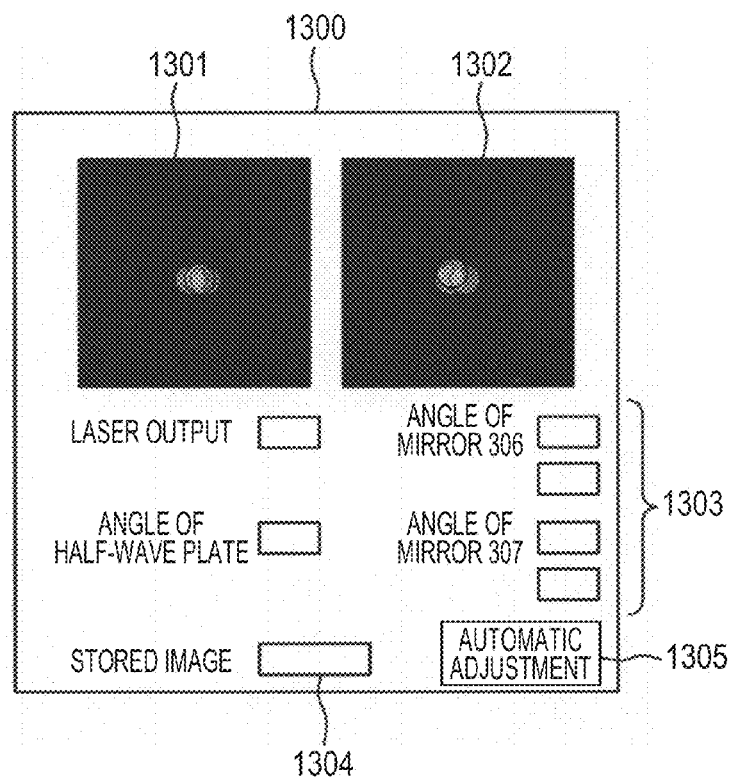
FIG. 13 is a front view of a display screen illustrating a GUI that can manually set the angle of the mirror according to an embodiment of the present invention.

Furthermore, the pattern detected at the beam monitor 23 is allowed to be displayed through a GUI. FIG. 13 is an example of a GUI 1300, and the GUI 1300 is displayed on the display unit 55, for example. 1301 denotes an image detected at the beam monitor 23 in the laser light beam pattern monitoring mode, and 1302 denotes an image detected at the beam monitor 23 in the focus acquiring mode. Detected images and given recorded images stored in the control unit 53 can be displayed at the same time. In the displaying, desirably, the colors of a stored image and a detected image are changed, for example. Stored images are a previously adjusted image and a pattern obtained at the beam monitor 23 in setting the half-wave plate 301 by driving the rotation control mechanism 311 in the mode in which the pulse of light transmitted through the half-wave plate 301 is not divided, for example. The present adjusting state is determined based on the image and the pattern.

1303 denotes parameters used for adjustment. The parameters are the angle of the mirror 306, the angle of the mirror 307, laser power outputted from the laser light source 2, the angle of the half-wave plate 301 controlled at the rotation control mechanism 311, and so on. Moreover, 1304 denotes an interface of switching between stored images, and inputs stored image names. 1305 denotes an automatic adjustment button. This button is clicked through an external input interface such as a mouse and a track ball, for example, for automatic adjustment.

Figure 14:
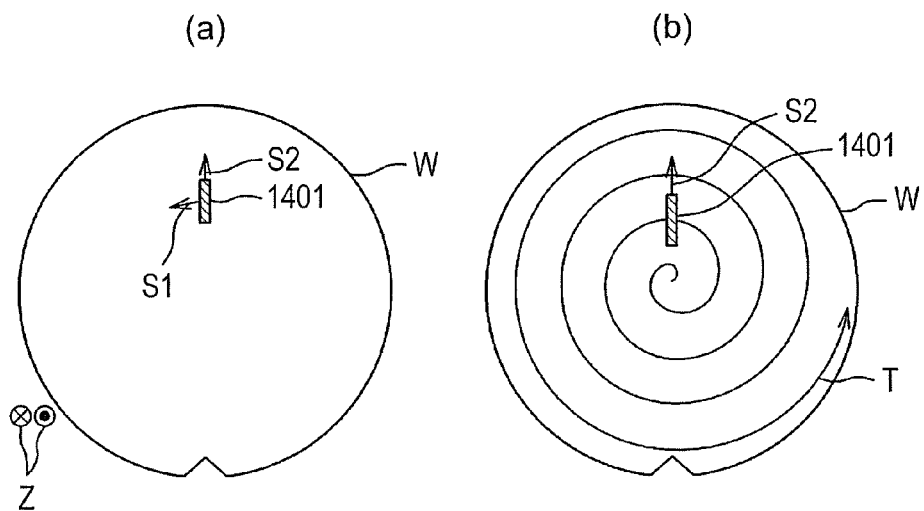
FIG. 14 is plan views of the detection visual field of a sample and a method for scanning the sample according to an embodiment of the present invention.

A typical method for inspecting a sample is illustrated in FIG. 14. As illustrated in (a), long, narrow light in one direction is applied to the sample W as denoted by 1401. As illustrated in (b), the luminous light 1401, which is long, narrow light in one direction, is moved in the radial direction of the sample W (in a direction S2) while rotating the sample W, so that the sample W is scanned on a helical track T for inspecting the entire surface of the sample. It is necessary to narrow the spot size of light in order to improve inspection sensitivity. However, it is necessary to narrow the line width of the spot size in the direction S1 in order to implement inspection at high throughput even in the state in which the speed of the stage rotating the sample W is low. Generally, the line width is increased in the direction S2. Therefore, it is necessary to strictly adjust the axis only in one direction at the pulse dividing unit 8.

On the other hand, when light of a small spot is inputted to the pulse dividing unit, a laser of a strong light intensity is prone to cause damage to optical devices such as a mirror and a polarizing beam splitter. Therefore, in order to make the damage smaller, there is a method in which a light spot is increased only in one direction, light is inputted to the pulse dividing unit, and the line width is increased in the other direction after dividing a pulse. This embodiment is illustrated in FIG. 15.

Figure 15:
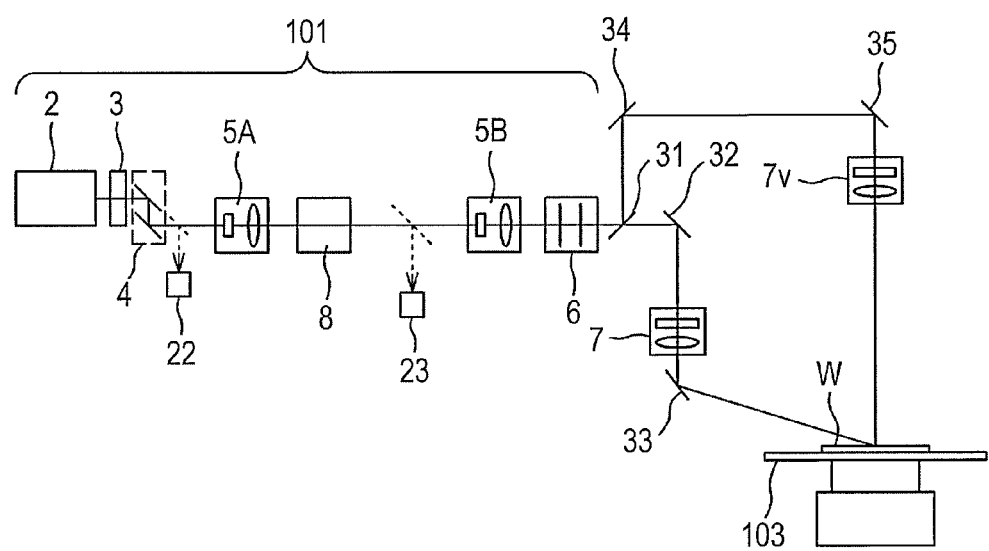
FIG. 15 is a block diagram of the schematic configuration of an illuminating unit of a defect inspection device illustrating an exemplary modification of the defect inspection device according to an embodiment of the present invention.

FIG. 15 illustrates a portion where the detection system and the processing system illustrated in FIG. 1 are omitted, in which the laser light beam expanding unit is split into 5A and 5B before and after the pulse dividing unit 8. 5A expands a laser light beam only in the direction corresponding to the direction S2 on the surface of the sample W. 5B expands the laser light beam only in the direction corresponding to the direction S1. With the configuration above, the area of the laser light beam is increased at the pulse dividing unit, and damage caused by a laser of a large power to optical components is reduced. Since the beam size is large on the sample in the direction S2, no problem arises because of fluctuations in the angular direction even though there are fluctuations in the angular direction more or less.

In the embodiment, adjustment is performed as described above, and the distribution comes close to an ideal Gaussian distribution particularly in the direction S1 on the sample surface. However, since light from a large number of different optical paths is applied, the distribution is not always in an ideal Gaussian distribution. Therefore, the pattern in the focus acquiring mode shot at the beam monitor 23 is used to estimate a profile on the sample surface, and parameters for processing signals are changed, so that the sensitivity difference between devices and reproducibility are secured. Suppose that a profile on the sample surface in the direction S1 is p(x). In this assumption, when a defect is small enough to the beam profile in the direction S1, the output s(t) of the defect determining unit 605 corresponding to defects obtained in a time series is matched with the profile p(x). Suppose that a signal converted into a time series signal p(x) is PS(t). In order to separate a defect from noise at the maximum, the profile PS(t) is convoluted for s(t). Therefore, the profile of the beam monitor 23 is used to form the high-pass filters 604a and 604b. The expected value of a defect signal obtained from above combination is proportional to an integral of the second power of PS(t). By this reason, a change of the profile of the beam monitor 23 causes a change of signal strength to be detected.

It is important for the inspection device to detect defects as well as to detect defect size. Generally, in the case where the defect size is small enough with respect to the wavelength of the illumination light, the defect is in a Rayleigh scattering region, and the scattered light quantity is proportional to the sixth power of the defect size. Therefore, the defect size is calculated based on the sixth root of the detected signal strength, and the calculated value is outputted as the detected defect size. However, in the case where the beam profile is varied at the pulse dividing unit 8, since the scattered light quantity is also proportional to the second power of PS(t) as well as the sixth power of Rayleigh scattering, it is necessary to normalize the beam profile. Therefore, the defect size is calculated as (Equation 1).

[Equation 1]

$$\text{Defect size} = K\, MAX(s(t) \otimes PS(t)) / \int PS(t)^2 \quad \text{(Equation 1)}$$

Here, K is a constant.

The defect size is determined using the equation at the defect determining units 605 and 606, so that it is possible to stably detect defects and to determine the size even in the case where the axis of the laser light beam is shifted at the pulse dividing unit 8 in the worst case.

Information about the determined defect size is displayed on the screen of the display unit 55.

INDUSTRIAL APPLICABILITY

The present invention can be applied to a defect inspection method and a device therefor that inspect micro defects on the surfaces of semiconductor substrates, thin film substrates, or the like, and determine and output defect types and defect size in order to maintain and improve the yields of products in the manufacturing line of semiconductor substrates, thin film substrates, or the like.

REFERENCE SIGNS LIST

2 Light source
3 Attenuator
4 Outgoing light adjusting unit
5 laser light beam expanding unit
6 polarization control unit
7 Light focusing control unit
7v Light focusing control unit
22 Beam monitor
23 Beam monitor
53 Control unit
54 Display unit
55 Input unit
101 Illuminating unit
102 Detecting unit
103 Stage unit
105 Signal processing unit
120 Optical axis of light

The invention claimed is:

1. A defect inspection device comprising:
a table unit on which a sample is placed, the table unit being rotatable;
a light source unit configured to emit a pulse laser;
an illumination optical unit configured to divide a pulse of the pulse laser emitted from the light source unit to apply the divided-pulse pulse laser to the sample placed on the table unit;
a detection optical unit configured to detect light reflected off the sample to which the divided-pulse pulse laser is applied by the illumination optical unit;
a signal processing unit configured to process an output signal from the detection optical unit detecting the reflected light to detect a defect on the sample; and
an output unit configured to output a result processed at the signal processing unit on a display screen,
wherein the illumination optical unit includes:
a pulse dividing unit configured to divide a pulse of the pulse laser emitted from the light source unit;
a first beam monitor unit configured to monitor a barycentric position of light intensity of the divided-pulse pulse laser emitted from the pulse dividing unit; and
a light intensity barycentric position adjusting unit configured to adjust the barycentric position of the light intensity of the divided-pulse pulse laser monitored at the first beam monitor unit.

2. The defect inspection device according to claim 1,
wherein the output unit displays an image of the divided-pulse pulse laser monitored at the first beam monitor unit on the display screen.

3. The defect inspection device according to claim 1,
wherein the illumination optical system unit further includes a laser light beam expanding unit configured to increase a diameter of a laser light beam of the divided-pulse pulse laser divided at the pulse dividing unit.

4. The defect inspection device according to claim 3,
wherein the pulse dividing unit is configured to include a pair of polarizing beam splitters and a pair of reflecting mirrors; and
angles of the pair of the reflecting mirrors are adjusted at the light intensity barycentric position adjusting unit.

5. The defect inspection device according to claim 4,
wherein the pulse dividing unit further includes a wave plate, in which the wave plate enables adjusting amplitudes of a first divided pulse and a second divided pulse of a pulse of a pulse beam emitted from the light source unit and transmitted through the pulse dividing unit.

6. The defect inspection device according to claim 5,
wherein the signal processing unit includes:
a filtering unit configured to apply low-pass filtering to an output signal from the detection optical system unit detecting light reflected off the sample to which the divided-pulse pulse laser of non-uniform light emitting intensity divided at the illumination optical system unit is applied; and a defect extracting unit configured to process the signal to which low-pass filtering is applied at the filtering unit to extract a defect.

7. The defect inspection device according to claim 4, wherein the illumination optical system unit further includes:

a deflection control unit configured to control a state of polarization of the divided-pulse pulse laser whose diameter of a laser light beam is increased at the laser light beam expanding unit;

an optical path switching unit configured to switch an optical path of the pulse laser whose polarization state is controlled at the deflection control unit;

an oblique illuminating unit configured to apply the pulse laser to the sample placed on the table unit in an oblique direction, an optical path of the pulse laser being switched to one side at the optical path switching unit, and the polarization state of the pulse laser being controlled; and a high angle illuminating unit configured to apply the pulse laser to the sample placed on the table unit from a high angle direction, the optical path of the pulse laser being switched to the other side at the optical path switching unit, and the polarization state of the pulse laser being controlled.

8. The defect inspection device according to claim 1, wherein the illumination optical unit further includes:

an outgoing light adjusting unit configured to adjust a beam position and a beam traveling direction of the pulse laser emitted from the light source unit; and a second beam monitor unit configured to monitor a position and an angle of a pulse laser transmitted through the outgoing light adjusting unit and entering the pulse dividing unit.

9. A defect inspection method comprising:

dividing a pulse of a pulse laser emitted from a light source;

applying the divided-pulse pulse laser to a surface of a sample moving in one direction while rotating the divided-pulse pulse laser;

detecting light reflected off the sample to which the divided-pulse pulse laser is applied;

processing a signal detecting the reflected light to detect a defect on the sample; and outputting information about the detected defect on a display screen, wherein a barycentric position of light intensity of the divided-pulse pulse laser is monitored; and the barycentric position of the light intensity of the monitored divided-pulse pulse laser is adjusted.

10. The defect inspection method according to claim 9, wherein an image of the monitored divided-pulse pulse laser is displayed on a screen; and the barycentric position of the light intensity of the divided-pulse pulse laser is adjusted based on the image of the divided-pulse pulse laser displayed on the screen.

11. The defect inspection method according to claim 9, wherein a diameter of a laser light beam of the divided-pulse pulse laser is increased and the divided-pulse pulse laser is applied to a surface of the sample.

12. The defect inspection method according to claim 11, wherein the division of the pulse is performed using an optical system configured to include a pair of polarizing beam splitters and a pair of reflecting mirrors; and the adjustment of the barycentric position of the light intensity is performed by adjusting angles of the pair of the reflecting mirrors.

13. The defect inspection method according to claim 12, wherein the division of the pulse is performed by adjusting amplitudes of a first divided pulse and a second divided pulse to be almost equal, the first divided pulse and the second divided pulse being pulses whose pulse of a pulse beam emitted from the light source unit is divided.

14. The defect inspection method according to claim 13, comprising:

switching an optical path of the divided-pulse pulse laser whose diameter of the laser light beam is increased; and applying the divided-pulse pulse laser to the surface of the sample by oblique illumination that applies the divided-pulse pulse laser to the sample from an oblique direction or by high angle illumination that applies the divided-pulse pulse laser to the sample from a high angle direction.

15. The defect inspection method according to claim 13, comprising:

applying low-pass filtering to a detected signal that light-reflected off the sample to which the divided-pulse pulse laser of non-uniform light emitting intensity is applied; and processing the signal to which the low-pass filtering is applied to extract a defect.

16. The defect inspection method according to claim 9, wherein a beam position and a beam traveling direction of the pulse laser emitted from the light source are adjusted; and a position and an angle of the pulse laser are monitored before dividing a pulse of the pulse laser whose beam position and beam traveling direction are adjusted.

* * * * *